United States Patent [19]

Takahashi et al.

[11] Patent Number: 4,595,485
[45] Date of Patent: Jun. 17, 1986

[54] LIMITING ELECTRIC CURRENT TYPE OXYGEN SENSOR

[75] Inventors: Hideaki Takahashi; Haruyoshi Kondo; Keiichi Saji; Kiyoharu Hayakawa; Takashi Takeuchi, all of Aichi, Japan

[73] Assignee: Kabushiki Kaisha Toyota Chuo Kenkyusho, Aichi, Japan

[21] Appl. No.: 775,741

[22] Filed: Sep. 13, 1985

Related U.S. Application Data

[63] Continuation of Ser. No. 589,503, Mar. 14, 1984, abandoned.

[30] Foreign Application Priority Data

Mar. 14, 1983 [JP] Japan .................. 58-40630

[51] Int. Cl.$^4$ .......................................... G01N 27/56
[52] U.S. Cl. ................... 204/406; 204/192 C; 204/192 SP; 204/408; 204/425
[58] Field of Search ............... 204/425, 426, 1 S, 406, 204/408, 192 C, 192 SP; 236/78 D

[56] References Cited

U.S. PATENT DOCUMENTS

| | | |
|---|---|---|
| 3,240,428 | 3/1966 | Umrath .................. 236/78 D |
| 3,946,297 | 3/1976 | Bechtel .................. 236/78 D X |
| 4,040,929 | 8/1977 | Bauer et al. .................. 204/426 |
| 4,207,159 | 6/1980 | Kimura et al. .................. 204/425 |
| 4,219,399 | 8/1980 | Gruner et al. .................. 204/428 X |
| 4,254,906 | 3/1981 | Hayes .................. 236/78 D |
| 4,292,158 | 9/1981 | Müller et al. .................. 204/425 X |
| 4,419,190 | 12/1983 | Dietz et al. .................. 204/1 T |
| 4,500,412 | 2/1985 | Takahashi et al. .................. 204/425 |
| 4,505,805 | 3/1985 | Mase et al. .................. 204/425 |
| 4,510,036 | 4/1985 | Takeuchi et al. .................. 204/425 |

FOREIGN PATENT DOCUMENTS

| | | | |
|---|---|---|---|
| 2348328 | 4/1975 | Fed. Rep. of Germany | 236/78 D |
| 2355246 | 5/1975 | Fed. Rep. of Germany | 236/78 D |
| 9034 | 1/1978 | Japan | 236/78 D |
| 115490 | 10/1978 | Japan | 236/78 D |

OTHER PUBLICATIONS

M. Croset et al., J. Vac. Sci. Technol., vol. 14, No. 3, pp. 777–781, May/Jun. 1977.

W. T. Pawlewicz et al., Thin Solid Films, 94, pp. 31–45, (1982).

*Primary Examiner*—G. L. Kaplan

[57] ABSTRACT

A limiting electric current type oxygen sensor comprising a first electrode of a gas-permeable film, a thin solid electrolyte film which is crystallized along one direction to decrease resistance and which has a thickness falling in the range between 0.1 μm and 30 μm, and a second electrode of a gas-permeable film sequentially formed on an electrically insulating substrate. This limiting electric current type oxygen sensor is also provided with a porous coating layer or a dense coating layer. The porous coating layer made of $Al_2O_3$, $SiO_2$, spinnel, SiC, $Si_3N_4$ and etc., has a porosity of not more than 30% and a thickness of not less than 1 μm, and serves as a gas diffusion flow rate-determining portion. The dense coating layer serves to control a gas permeation path such that either the first electrode or the substrate is used as the gas diffusion flow rate-determining portion.

31 Claims, 26 Drawing Figures

LIMITING ELECTRIC CURRENT TYPE OXYGEN SENSOR

This is a continuation of application Ser. No. 589,503 filed Mar. 14, 1984 and now abandoned.

BACKGROUND OF THE INVENTION

1. Field of the Invention

The present invention relates to a limiting electric current type oxygen concentration sensor as one of oxygen concentration measuring sensors such as a magnetic type sensor utilizing the paramagnetic property of oxygen and zirconia type and galvanic cell type sensors which utilize the oxygen ionic conductivity.

2. Description of the Prior Art

Electrodes are formed to both major surfaces of an oxygen ionic conductive solid electrolyte plate, and an electric current flows through the solid electrolyte plate to move the oxygen for one direction. When a hermetic cover is provided for one of the electrodes, oxygen is supplied at a predetermined flow rate from an external source inside the cover, and a voltage is applied across two electrodes using the electrode at the side of the cover as a cathode, movement of oxygen ions can be effected in proportion to an amount of oxygen supplied thereto, so that an electric current flows from the anode to the cathode. The amount of oxygen flowing in the cover can then be calculated in accordance with the value of the electric current. The concentration of oxygen can be calculated if it is proportional to the flow rate thereof. The following sensor is conventionally proposed to serve as a limiting current type oxygen sensor which realizes the above-mentioned principle. Electrodes are formed to the upper and lower surfaces of a sintered solid electrolytic plate, and one of the electrodes is hermetically sealed with a cover. At the same time, an aperture is formed in a part of the cover such that the diffusion rate of oxygen in a gas to be measured and flowing therethrough serves as a determining factor such that the diffusion flow rate of oxygen is proportional to the concentration of oxygen. Alternatively, a porous coating layer is used in place of the cover with an aperture. In addition, electrodes are formed on inner and outer surfaces of a hollow cylindrical sintered body, and a coating is formed on an outer electrode such that the flow rate of oxygen gas is proportional to the concentration thereof. The sensor having the construction described above is heated by a heater to a temperature of 500° to 800° C. to get the oxygen gas ionized and conducted through the solid electrolytic plate. However, according to this conventional method, the oxygen concentration detecting device becomes large in size as a whole, and becomes complex in structure. Recently, a device having a sensor integrally formed with a heater has been proposed. However, the sensor of this type still presents the following drawbacks (a) The sensor as a whole must be heated to a high temperature to realize good ionic conduction and hence decrease an electric resistance of the sensor.

(b) Variations in apertures of the cover and the porosity of the porous coating layer result in deviations in characteristics of the sensor.

(c) A lot of power is required to heat the sensor since the sensor is large in size.

SUMMARY OF THE INVENTION

The present invention seeks to overcome the problems of the conventional limiting electric current type oxygen sensors described above, and has for its object to provide a compact limiting electric current type oxygen sensor wherein a measuring range is wide, good measuring characteristics can be obtained at a relatively low temperature, measurement stability is good, variations in the characteristics are small, and sensor size is small.

In order to achieve the above object of the present invention, there is provided a construction wherein sensor resistance is decreased, and at the same time, the diffusion flow rate of oxygen gas can be stably determined by oxygen diffusion.

The present invention provides a basic sensor construction obtained by sequentially stacking a first electrode, a thin solid electrolyte thin film and a second electrode on a substrate. The first and the second electrode are gas-permeable.

The thin solid electrolyte film has a specific orientation of crystal and has a thickness of 0.1 $\mu$m to 30 $\mu$m to get the decreased resistance of the sensor. The first and second electrodes are made of a Pt, Pd or Ag material, or an alloy containing Pt, Pd or Ag as a major constituent.

An oxygen gas flow rate-determining portion is provided in any one of the substrate, an electrode, or the gas-permeable coating. In order to detect the concentration of oxygen more precisely, it is necessary to add an impermeable coating layer so as to avoid gas diffusion flow from the cathode side.

On the other hand, when the rate-determining portion is constituted by the gas-permeable coating, the coating is preferably made of $Al_2O_3$, $SiO_2$, spinnel, SiC or $Si_3N_4$. The coating preferably has a thickness of 10 $\mu$m and a porosity of not more than 30%.

The substrate may comprise silicon, and necessary processing circuits such as a circuit for detecting a limiting electric current and converting the limiting electric current to a voltage, and an oxygen concentration detecting circuit such as a constant temperature control circuit for controlling a heating temperature to be constant may also be formed on the single silicon substrate having the oxygen concentration detecting circuit thereon.

DETAILED DESCRIPTION OF THE PREFERRED EMBODIMENTS (Thickness of Solid Electrolyte)

Figure 1:
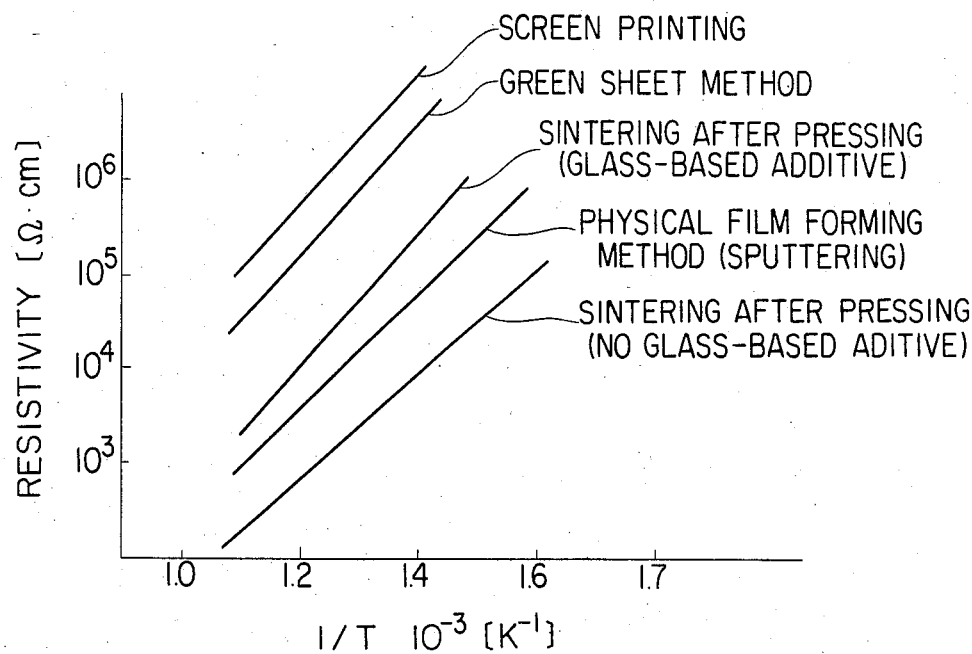
FIG. 1 is a graph showing resistivity-temperature characteristics of solid electrolytes prepared by various methods.

Dense solid electrolytes capable of allowing only oxygen ions to conduct therethrough can be prepared by sintering (including a green sheet method, screen printing and so on), and physicochemical methods (e.g., sputtering, vacuum evaporation, and chemical vapor deposition (CVD) etc.). The physicochemical methods are used in the present invention. The solid electrolytes ($Y_2O_3$ stabilized $ZrO_2$) prepared by these methods have resistivity-temperature characteristics as shown in FIG. 1. As is apparent from FIG. 1, resistivities of the solid electrolytes greatly differ in accordance with the manufacturing methods. In order to obtain a dense solid electrolyte having good ionic conductivity, a glass-based material for sintering acceleration should not be added to the electrolyte material. The oxide material is sintered after pressing. However, according to this method, sintering conditions become onerous such that the oxide material must be sintered at a temperature of 2,000° C. in an outer atmosphere for several hours. On the other hand, in sintering using a glass-based additive in a method (e.g., sintering after pressing, green sheet method, screen printing), the solid electrolyte can be sintered at a temperature of not higher than 1,600° C. to obtain a sufficiently dense sintered body. In this case, however, the resistivity of the resultant sintered body is greatly increased. In the methods described above, the thickness of the resultant solid electrolyte can be decreased to obtain a low electric resistance. However, it is impossible to decrease the thickness of the solid electrolyte to be less than 50 $\mu$m due to a difficulty of manufacture. On the other hand, in thin solid electrolyte films prepared by the physicochemical methods (e.g., sputtering, vacuum evaporation and CVD), a good crystal structure is obtained depending on a manufacturing condition, so that a dense thin solid electrolyte film can be prepared. The resistivity of a resultant solid electrolyte comprising a thin solid electrolyte film is only slightly higher than that obtained by the method wherein the glass-based additive is not used. As a result, a thin solid electrolyte film having a relatively low resistivity can be obtained. In addition, the film thickness can fall within the wide range between 10 $\mu$m and several tens of angstroms. Therefore, the electric resistance of the electrolyte can be reduced theoretically to 1/100 to 1/500 of that of the electrolyte obtained by conventional sintering wherein the thickness of the electrolyte is greatly decreased.

However, in practice, the small thickness range attainable is limited. Moreover, a thin film of poor quality cannot decrease the electric resistance of the resultant solid electrolyte. In addition to these disadvantages, stable operation cannot be expected. It is important to form a thin crystalline film which has good quality and high stability. It is also important to find an optimal thickness range of the film. The relationship between the resistances and the thicknesses of the thin solid electrolyte films at an ambient temperature of 700° C. is illustrated in FIG. 2.

Figure 2:
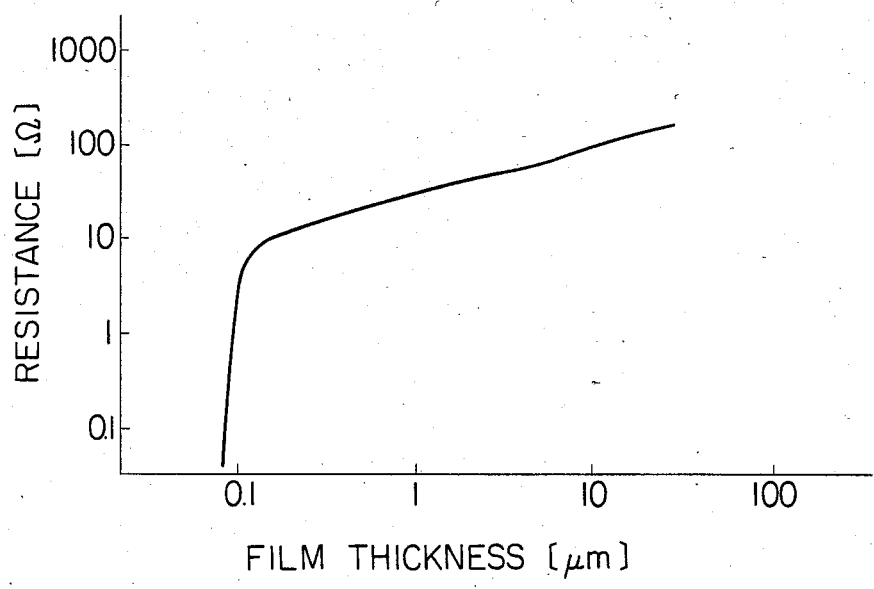
FIG. 2 is a graph showing the resistance of a sample as a function of the thickness of the solid electrolyte, when a sample of a size of 3×3 mm with platinum electrodes each having a size of 2×2 mm is measured in an air at a temperature of 700° C.

Referring to FIG. 2, when a film thickness of each solid electrolyte is decreased to be not more than 0.1 μm, its resistance is abruptly decreased, so that the thin film is short-circuited. However, when the thickness of the film is not less than 0.1 μm, the resistance is substantially proportional to the film thickness. When the thickness is increased, the resistance is also increased. Therefore, the film thickness must be not less than 0.1 μm. In addition, in practice, the deposition rate of the film according to the physicochemical method is as low as several tens of angstroms to several hundreds of angstroms per minute. Furthermore, when the film thickness is increased, the resistance becomes excessively high, and a detected electric current becomes small, resulting in inconvenience. Therefore, the film thickness preferably falls within the range between 0.1 μm to 30 μm.

(Film Quality of Solid Electrolyte)

Figure 3:
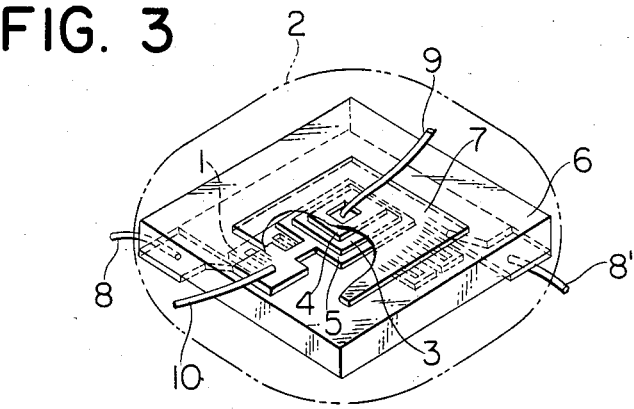
FIG. 3 is a perspective view showing the construction of a limiting electric current type oxygen sensor according to an embodiment of the present invention.

FIG. 3 shows a construction of a limiting electric current type oxygen sensor according to an embodiment of the present invention.

A cathode 5 of a platinum film, a thin solid electrolyte film 3 of $Y_2O_3$ stabilized $ZrO_2$, an anode 4 of a platinum film, and a thin $Al_2O_3$ coating 7 having an opening to expose part of the anode 4 are sequentially formed on one major surface of an $SiO_2$ insulating substrate 6, thereby constituting a sensor section. A heater 1 of a thin Pt film in a zigzag pattern is formed on the opposing major surface of the insulating substrate 6 to heat the sensor section. The entire structure is covered with a porous coating 2 to protect the structure. Lead wires 8 and 8' are connected to the heater 1, and lead wires 9 and 10 are respectively connected to the anode 4 and the cathode 5. The lead wires 8, 8', 9 and 10 comprise Pt wires each having a diameter of 50 μm.

In the limiting electric current type oxygen sensor using the thin solid electrolyte film, it is desired to form a dense thin film which has a low electric resistance and though which only oxygen ions are conducted. In order to clarify the conditions for these requirements, the following test was performed.

A solid electrolyte ($Y_2O_3$ stabilized $ZrO_2$) was deposited by a high-rate sputtering apparatus on an upper surface of a quartz substrate (having a size of 20×20×0.5 mm) for about 2 to 4 hours under the following conditions:

Distance between target and substrate: 75 mm
Sputtering atmosphere:
(1) Ar atmosphere at a pressure of $4 \times 10^{-3}$ Torr at Ar flow rate og 20 cc/min
(2) 10%-$O_2$/Ar atmosphere at a pressure of $4 \times 10^{-3}$ Torr
Input power: ~300 W
Substrate temperature: 20° C., 200° C., 500° C., 700° C., 1,000° C.
Sputtering time: 4 to 8 hours X-ray diffraction analysis was performed for each of the thin sputtered $Y_2O_3$ stabilized $ZrO_2$ films. It was found that different crystal structures were obtained in accordance with different gas atmospheres and different substrate temperatures.

TABLE 1

| Sputtering atmosphere | Substrate heating temperature (°C.) | Orientation of crystal |
|---|---|---|
| ① Ar gas | 200 or lower | Amorphous |
| | 200 to 500 | [111] + [220] fibrous texture |
| | 500 or higher | Weak [111] fibrous texture |
| ② Ar + $O_2$ gas | 200 or lower | Amorphous |
| | 200 to 350 | Weak [111] fibrous texture |
| | 350 or higher | Strong [111] fibrous texture |

Figure 4:
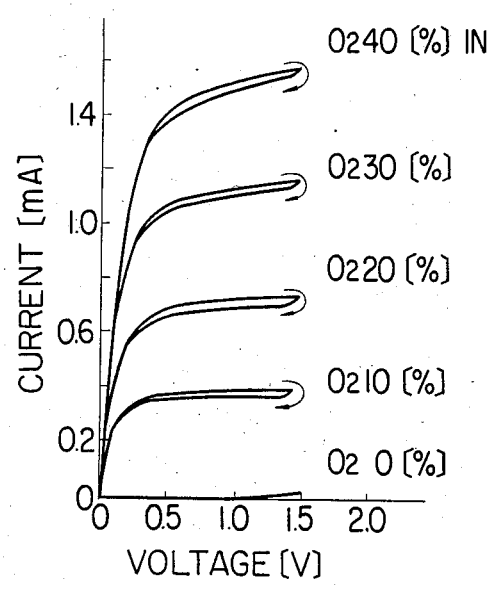
FIG. 4 is a graph showing the current-voltage characteristic curves of the oxygen sensor of FIG. 3 when the concentration of $O_2$ contained in $N_2$ gas is used as a parameter.
Figure 5:
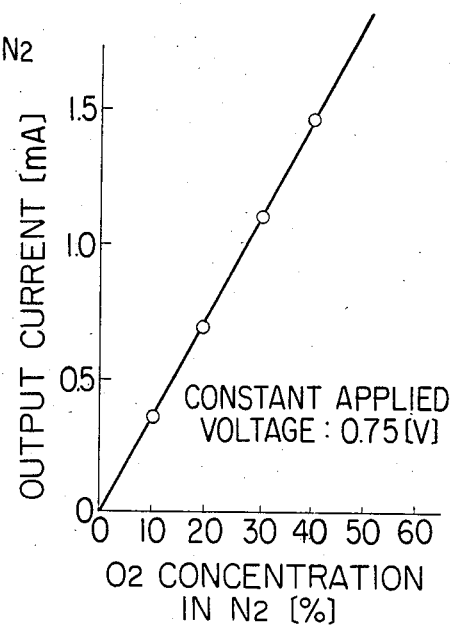
FIG. 5 is a graph showing the characteristics of the oxygen concentration vs. current when the sensor is kept at a constant temperature of 700° C. and a voltage of 0.75 V is applied thereto.

These resultant films were annealed in the outer atmosphere at a temperature of 1,000° C. for 3 hours, and were then subjected to X-ray diffraction again to check changes in crystal structure following annealing. As a result, in the amorphous film prior to annealing, upon annealing crystal growth slightly occurs along the orientation [111] and [220] of crystal. However, when the crystal is grown along the specific direction, no change occurs in the crystal structure even if annealing is performed. A sensor having a multilayer structure was prepared, as shown in FIG. 3. The current-voltage characteristics of the sensor were examined using the concentration of $O_2$ gas in $N_2$ gas as a parameter. The results are shown in FIG. 4. In addition, the characteristics of the oxygen concentration vs. current were examined when a constant voltage of 0.75 V was applied to the sensor shown in FIG. 3. In this case, the sensor was heated to a constant temperature of 700° C. An output current increases in proportion to the oxygen concentration at the beginning of heating, as shown in FIG. 5. In addition, in order to examine the stability of the sensor, a change in output current from the sensor as a function of time was examined in an air while the sensor was heated at the constant temperature of 700° C. Results are shown in Table 2.

TABLE 2

Stability test for different film qualities

| Film quality | Before test (mA) | After 50 hours | After 200 hours | After 500 hours | Evaluation |
|---|---|---|---|---|---|
| Amorphous | 0.8 | 20% output current increase | 40% output current increase | 64% output current increase | x |
| Weak [111] fibrous texture; oriented | 1.1 | 3% output current increase | 4% output current increase | 5% output current increase | o |
| Strong [111] fibrous texture; oriented | 1.3 | 2% output current increase | 3% output current increase | 3% output current increase | o |
| [111] + [220] fibrous texture; oriented | 1.2 | 1% output current increase | 1% output current increase | 1% output current increase | o |

According to Table 2, in a thin amorphous solid electrolyte film, the output current increases over time, so that great changes occur over time. However, in a thin solid electrolyte film whose crystal is grown in a specific orientation, the change in output current is small, so that stable operation can be obtained.

It is necessary to use as an oxygen sensor material a film havinq a given orientation of crystal.

In this embodiment, the $Y_2O_3$ stabilized $ZrO_2$ material is used as the thin solid electrolyte film material. However, a stabilizer such as $Yb_2O_3$, $Gd_2O_3$, MgO, CaO, and $Sc_2O_3$ may be added to $ZrO_2$. Alternatively, $Bi_2O_3$ containing $Y_2O_3$, $Er_2O_3$, $WO_3$ or the like may be used. In these cases, it is also necessary to prepare a film having a specific direction of crystal.

(Electrode Material)

Figure 6:
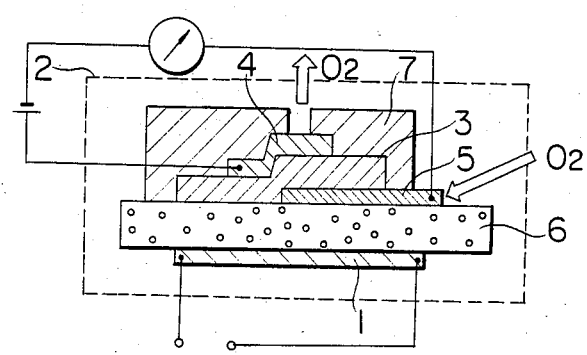
FIG. 6 is a sectional view of a limiting electric current type oxygen sensor according to another embodiment wherein the diffusion flow rate of the oxygen gas is determined by a cathode member.
Figure 7:
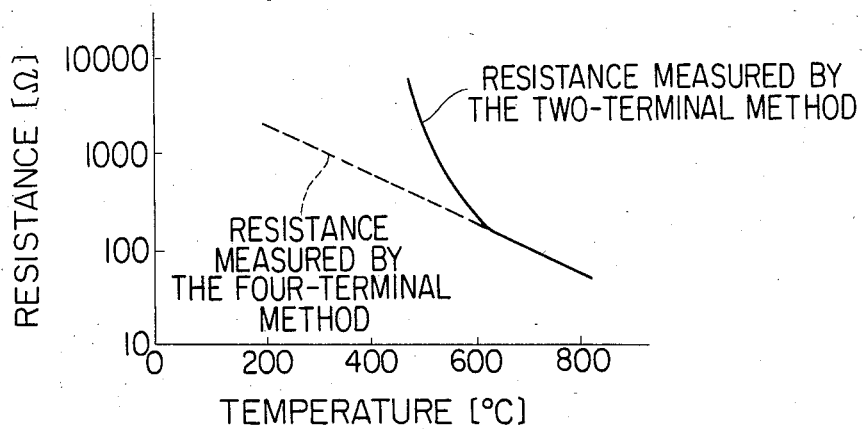
FIG. 7 is a graph showing the resistance-temperature characteristics of the solid electrolyte.
Figure 8:
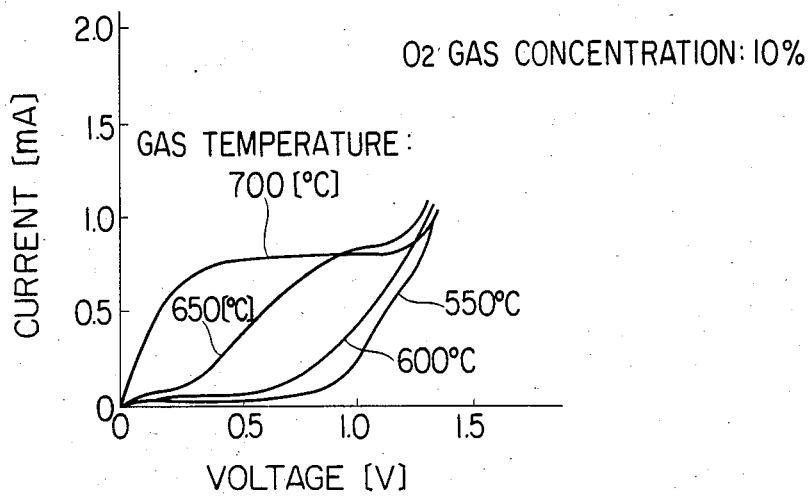
FIG. 8 is a graph showing the current-voltage characteristic curves in a 10% oxygen gas atmosphere when the gas temperature is used as a parameter.

FIG. 6 is a sectional view of a limiting electric current type oxygen sensor according to a second embodiment of the present invention. This sensor has a construction wherein a diffusion flow rate of oxygen gas can be determined by a cathode 5 by using a dense coating 7. The oxygen gas is converted by the cathode 5 to oxygen ions. These oxygen ions are conducted through a thin solid electrolyte film 3 and are moved to an anode 4. The oxygen ions are converted to oxygen gas by an anode 4. The oxygen gas passes through the coating 7. In this case, the electrode members must be brought into ohmic contact with the thin solid electrolyte film. If an optimal electrode material is not selected, the following phenomenon occurs, thereby degrading the temperature characteristics. More particularly, the electrodes are formed to the thin solid electrolyte film, and the resistance-temperature characteristics are examined by a four-terminal method and a two-terminal method. The results are shown in FIG. 7. In addition, the current-voltage characteristics of the sensor are shown in FIG. 8 when the sensor is placed in 10% oxygen gas atmosphere and the gas temperature is used as a parameter. According to the results shown in FIG. 7, the resistance measured by the four-terminal method greatly differs from that measured by the two-terminal method when the gas temperature is decreased. The resistance measured by the four-terminal method indicates that of the solid electrolyte, so that a difference between the resistances measured by the four- and two-terminal methods indicates a resistance at an interface of the electrodes and the electrolyte. Therefore, as shown in FIG. 7, since the resistance measured by the two-terminal method becomes greater than that measured by the four-terminal method when the sensor temperature decreases, the interface resistance increases. In addition, according to the results in FIG. 8, the current-voltage characteristics of the sensor greatly change in accordance with a change in gas temperature. This is because the electrode interface resistance is affected.

The conditions for the electrode material lie in the requirement for a material that can effectively convert oxygen gas to oxygen ions and can cause the oxygen ions to effectively move through the solid electrolyte. In other words, the electrode material must have an ohmic contact with the solid electrolyte. In order to determine which material is most proper as the electrode material, the following samples were prepared and their characteristics were measured.

(A) Samples (a) Sample for examining current-voltage characteristics at a constant oxygen concentration Sample obtained such that an electrode of each of various electrode materials, a $Y_2O_3$ stabilized $ZrO_2$ film, another electrode of each of various electrode materials and the coating are sequentially deposited on an alumina substrate (FIG. 6)

(h) Sample for measuring resistance by the two-terminal method

Sample obtained such that an electrode of each of various electrode materials, a thin $Y_2O_3$ stabilized $ZrO_2$ film and another electrode of each of various electrode materials are sequentially deposited on an $Al_2O_3$ substrate (c) Sample for measuring resistance by the four-terminal method Sample obtained such that a thin $Y_2O_3$ stabilized $ZrO_2$ stripe is formed on an alumina substrate, and four electrodes are connected to the film at equal intervals (B) Measuring Method of Characteristics (a) A current is detected and measured at a gas temperature of 500° C. in a 5% oxygen gas atmosphere while a voltage of 0.5 V is applied to the sample.

(b) A response time is measured at a gas temperature of 500° C. when an electric current changes up to 50% while an oxygen concentration changes from 0% to 5% at a constant voltage of 0.5 V.

(c) An electrode-electrolyte interface resistance is measured at a gas temperature of 500° C. in accordance with a difference between resistances of the sample which are measured by the two- and four-terminal methods.

These results are summarized in Table 3.

TABLE 3

Detected current/response/interface resistance characteristics for different electrode materials

| Electrode material | Detected current (mA) | Response time (msec) | Electrode-electrolyte interface resistance (Ω) | Evaluation |
|---|---|---|---|---|
| Pt | 0.15 | 500 | 120 | Δ |
| Pt:Rh = 9:1 | 0.1 | 650 | 210 | Δ |
| Pt:Rh = 5:5 | 0.05 | 3,000 | 230 | x |
| Pd | 0.25 | 90 | 40 | o |
| Pt:Pd = 9:1 | 0.2 | 100 | 70 | o |
| Pt:Pd = 5:5 | 0.2 | 100 | 83 | o |
| Rh | 0.05 | 3,000 | 340 | x |
| Ag | 0.3 | 70 | 50 | o |
| Pt:Ag = 9:1 | 0.3 | 70 | 60 | o |
| Pt:Ag = 5:5 | 0.3 | 70 | 63 | o |
| Cr | 0.05 | 4,000 | 410 | x |
| Pt:Cr = 5:5 | 0.1 | 700 | 200 | Δ |
| Pt:Ni = 9:1 | 0.17 | 600 | 160 | Δ |
| Ag:Au = 9:1 | 0.25 | 200 | 113 | Δ |
| Pt:Au = 9:1 | 0.20 | 400 | 154 | Δ |
| Au | 0.06 | very poor response | 1,300 | x |

According to Table 3, the detected current, response time and interface resistance greatly vary in accordance with different electrode materials. It is found that an optimal electrode material having a low interface resistance is Pt, Pd or Ag, or an alloy containing Pt, Pd or Ag as a major constituent. (Substrate as Oxygen Gas Rate-Determining Portion)

Figure 9:
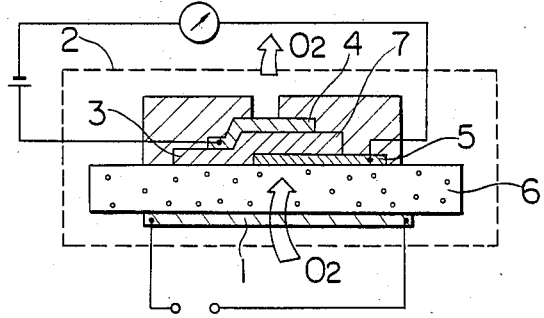
FIG. 9 is a sectional view of a limiting electric current type oxygen sensor according to still another embodiment wherein the diffusion flow rate of the oxygen gas is determined by the substrate.

FIG. 9 is a sectional view showing a limiting electric current type oxygen sensor according to a third embodiment of the present invention wherein the diffusion-flow rate of oxygen gas is determined by substrate 6 for supporting a thin solid electrolyte film. This sensor has a sensor section having a construction wherein heater 1 is formed on one major surface of the substrate 6, and cathode 5, thin solid electrolyte film 3, anode 4 and impermeable coating 7 having an aperture corresponding to part of the anode 4 are formed on the other major surface of the substrate 6. The entire structure is covered with a porous coating. According to this embodiment, it is important to properly select the substrate material for determining the diffusion-flow rate of oxygen gas. Different limiting electric current type oxygen sensors having the structure shown in FIG. 9 are prepared using different substrate materials having different gas permeabilities. The gas permeability was measured by the quantity of air flowing through each substrate having a diameter of 20 mm and a thickness of 0.3 mm while an air pressure of 1 kg/cm$^2$ acted on one of the major surfaces of the substrate.

Figure 10:
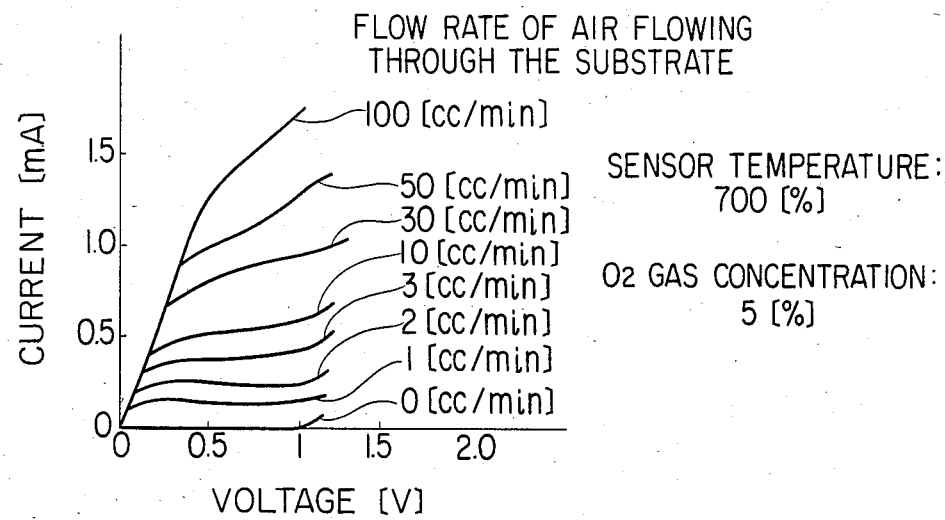
FIG. 10 is a graph showing the current-voltage characteristic curves when the quantity of air permeating through the substrate is used as a parameter.

The current-voltage characteristics of sensors having different substrates were measured at a sensor temperature of 700° C. and a 5% oxygen concentration. Results are shown in FIG. 10 wherein the quantity of air flowing through the substrate is used as a parameter. According to the results of FIG. 10, the oxygen gas rate-determination varies in accordance with a change in the air permeability rate. When a substrate material has an air permeability rate of not more than 3 cc/min, even if the voltage changes, the limiting electric current characteristic becomes substantially constant, thereby obtaining sufficient electrical characteristics of the limiting electric current type oxygen sensor. In practice, a material having an air permeability rate of up to 50 cc/min can be used as a substrate material.

The substrate material can comprise $Al_2O_3$, $SiO_2$, SiC or an $Si_3N_4$-based material.

(Coating as Oxygen Gas Rate-Determining Portion)

Figure 11:
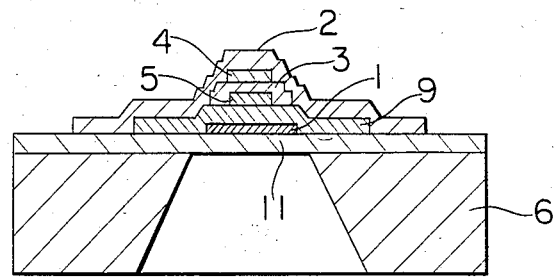
FIG. 11 is a sectional view of a limiting electric current type oxygen sensor according to still another embodiment wherein the diffusion flow rate of the oxygen gas is determined by the coating.

FIG. 11 is a sectional view showing a limiting electric current type oxygen sensor according to a fourth embodiment of the present invention wherein the diffusion-flow rate of oxygen gas is determined by a coating. The sensor of this type has a construction wherein thin $SiO_2$ insulating film 11, a heater 1, an $Al_2O_3$ or $SiO_2$ insulating film 9, cathode 5, thin solid electrolyte film 3, anode 4, and coating 2 are sequentially formed on one major surface of an Si substrate 6. In order to minimize power consumption of the sensor, a portion of the silicon substrate which corresponds to the sensor section may be etched by anisotropic etching from the other major surface of the Si substrate 6. According to this fourth embodiment of the present invention, the coating greatly influences the sensor characteristics. The relation between the thickness and porosity of the coating, and the sensor characteristics was examined in the following manner.

(a) An $Al_2O_3$ target material was sputtered as coating 2 by a high-rate sputtering apparatus. The current-voltage characteristics of the coating 2 were examined in a 5% $O_2$ gas atmosphere with the thickness of the $Al_2O_3$ film being used as a parameter. The results are shown in FIG. 12.

Figure 13:
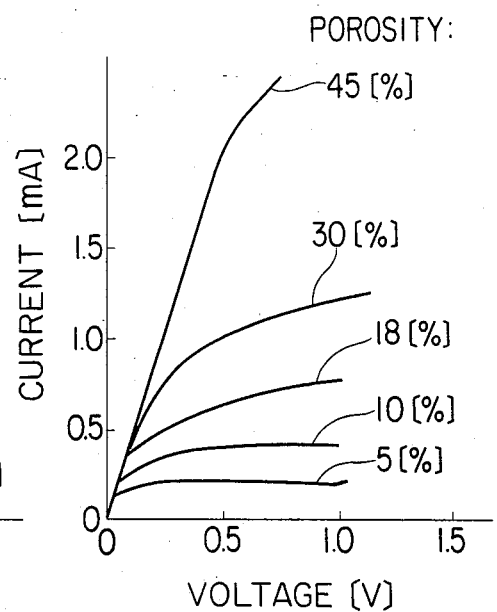
FIG. 13 is a graph showing the current-voltage characteristic curves of the oxygen sensor of FIG. 11 in a 5% oxygen gas atmosphere when the porosity of the coating is used as a parameter.

(b) An $Al_2O_3$-based paste having different $Al_2O_3$ particle sizes was coated as the coating 2 by screen printing to a thickness of about 10 μm. The current-voltage characteristics of the coating 2 were measured in a 5% $O_2$ gas atmosphere when a porosity of the coating was used as a parameter. The results are shown in FIG. 13.

Figure 12:
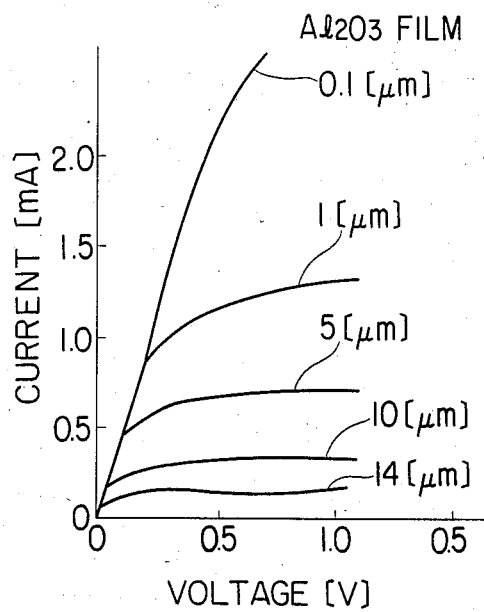
FIG. 12 is a graph showing the current-voltage characteristic curves of the oxygen sensor of FIG. 11 in a 5% oxygen gas atmosphere when the coating comprises an $Al_2O_3$ film and the film thickness is used as a parameter.

According to FIG. 12, when the coating has a porosity of not less than 5 μm and a porosity of not more than 10%, an electric current does not substantially change even if a voltage varies between 0.2 V and 1 V. This shows that the diffusion flow rate of oxygen gas can be properly determined. In practice, the coating thickness is preferably not less than 1 μm, as shown in FIG. 12, and its porosity is preferably not more than 30%, as shown in FIG. 13. Any one of the materials $Al_2O_3$, $SiO_2$, spinnel, SiC or $Si_3N_4$ can be used as a coating material.

(Solid Electrolyte Material)

A solid electrolyte material can be properly selected to decrease the electric resistance of the sensor and provide good oxygen ionic conduction, as an alternative to decreasing the thickness of the thin solid electrolyte film as previously described.

Figure 14:
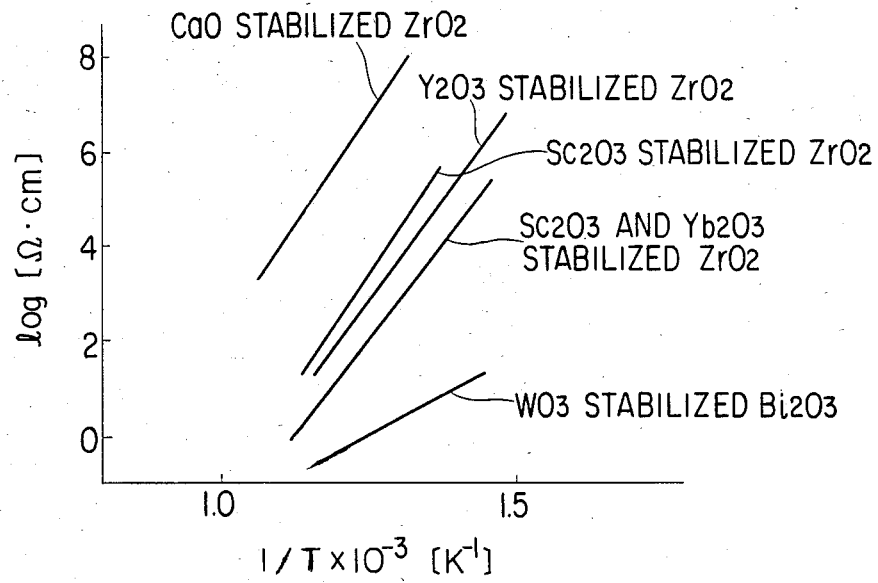
FIG. 14 is a graph showing the resistivity-temperature characteristics of various solid electrolytes prepared by sintering.
Figure 15:
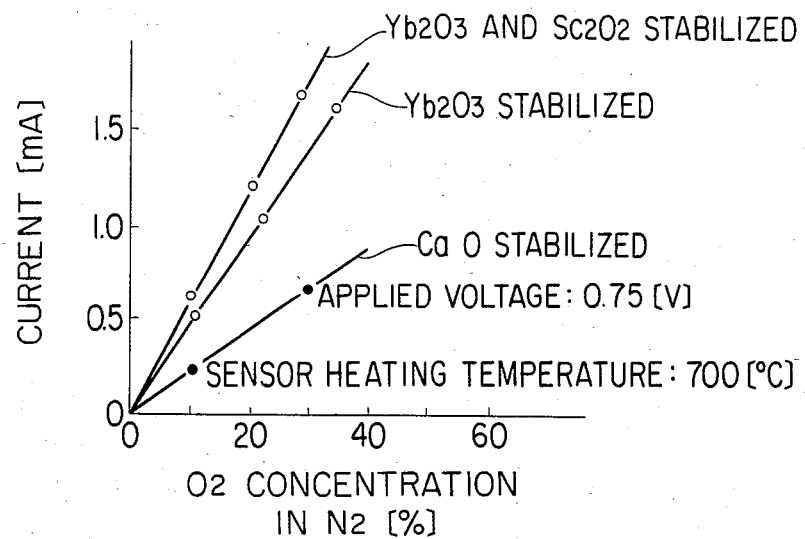
FIG. 15 is a graph showing the characteristics of the voltages vs. oxygen concentrations of sensors obtained by using the above-mentioned various solid electrolytes when the sensors are heated to a temperature of 700° C. and a voltage of 0.75 V is steadily applied thereto.
Figure 16:
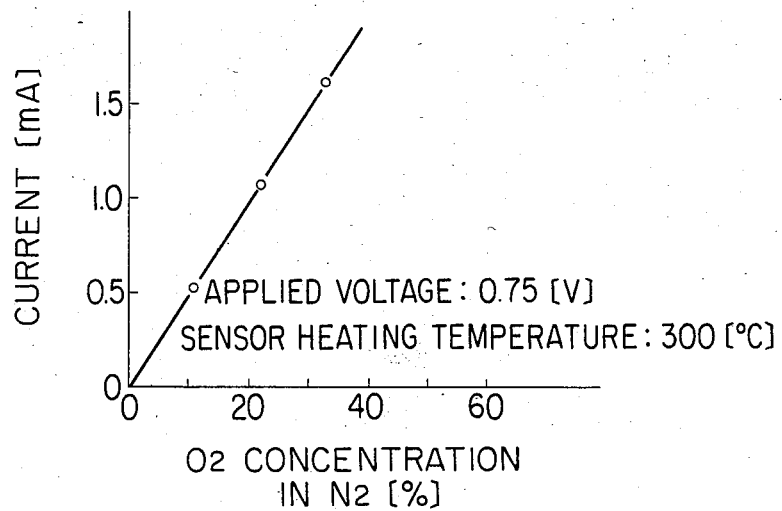
FIG. 16 is a graph showing the characteristics of the current vs. oxygen concentration of a sensor prepared such that a solid electrolyte is obtained by adding $WO_3$ to $Bi_2O_3$, when the sensor is heated to a temperature of 300° C. and a voltage of 0.75 V is applied thereto.

FIG. 14 shows the resistivity-temperature characteristics of various types of solid electrolytes. Solid electrolytes such as $Yb_2O_3$ stabilized $ZrO_2$, $Sc_2O_3$ and $Yb_2O_3$ stabilized $ZrO_2$ and $WO_3$ stabilized $Bi_2O_3$ were sputtered as the target materials to respectively prepare sensors with heaters in the same manner as for the type of sensor shown in FIG. 6. The relations between the oxygen concentrations and the electric currents were measured. The results are shown in FIGS. 15 and 16. FIG. 15 shows the relations between the currents and oxygen concentrations of a $Yb_2O_3$ stabilized $ZrO_2$ solid electrolyte and a ($Yb_2O_3$ and $Sc_2O_3$) stabilized $ZrO_2$ solid electrolyte when the sensors are heated to a temperature of 700° C. and a voltage of 0.75 V is applied thereto. FIG. 16 shows the relation between the current and oxygen concentration of a $WO_3$ stabilized $Bi_2O_3$ solid electrolyte when the sensor is heated to a temperature of 300° C. and a voltage of 0.75 V is applied thereto.

According to these results, the sensor temperature during operation can be greatly decreased when a proper solid electrolyte is selected. In addition, a high output current can be obtained. Therefore, in order to improve ionic conduction and increase the output current, the coating is preferably made of a material comprising $ZrO_2$ and as a stabilizer at least one of $Y_2O_3$, $Yb_2O_3$, $Gd_2O_3$ and $Sc_2O_3$, or a $Bi_2O_3$-material containing $Y_2O_3$, $Er_2O_3$ and/or $WO_3$.

(Shape of Substrate)

A thin solid electrolyte film having good crystallinity can be arbitrarily formed by a physicochemical method on any one of the substrates. The substrate or base may have a sheet-like shape (FIGS. 3, 6, 9, 11 and 19), a cylindrical shape (FIGS. 17 and 18), or a spherical shape. In this manner, the base is not limited to a specific shape.

Figure 17:
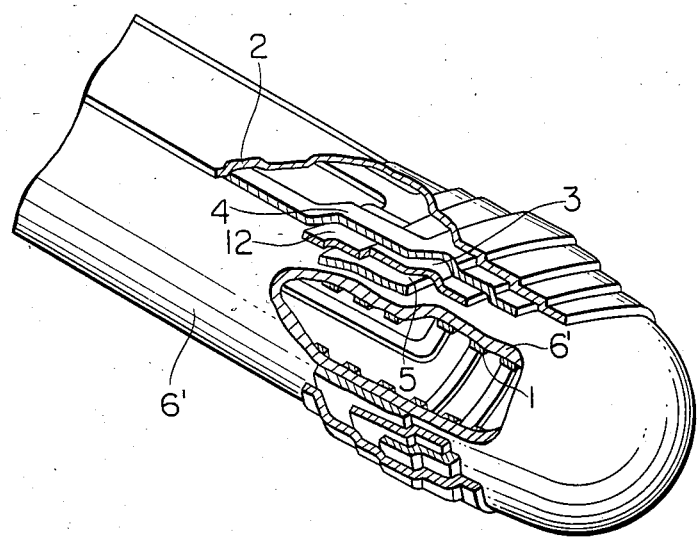
FIGS. 17 and 18 are partially cutaway perspective views showing limiting electric current type oxygen sensors having cylindrical substrates, respectively.
Figure 18:
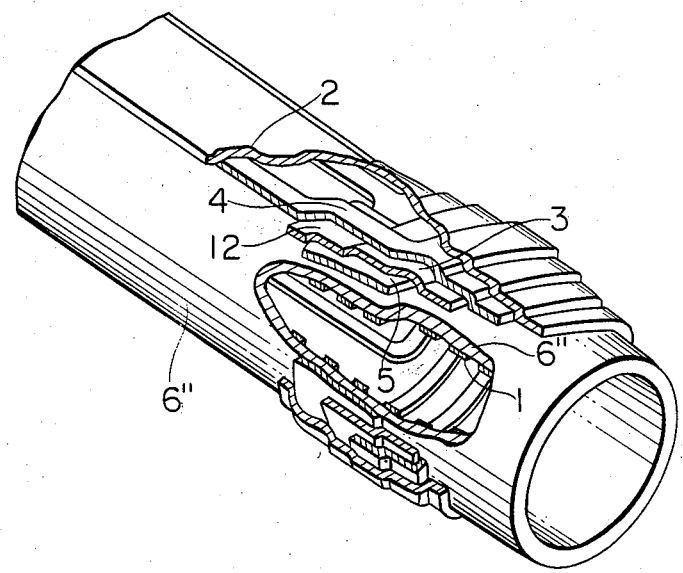
Figure 19:
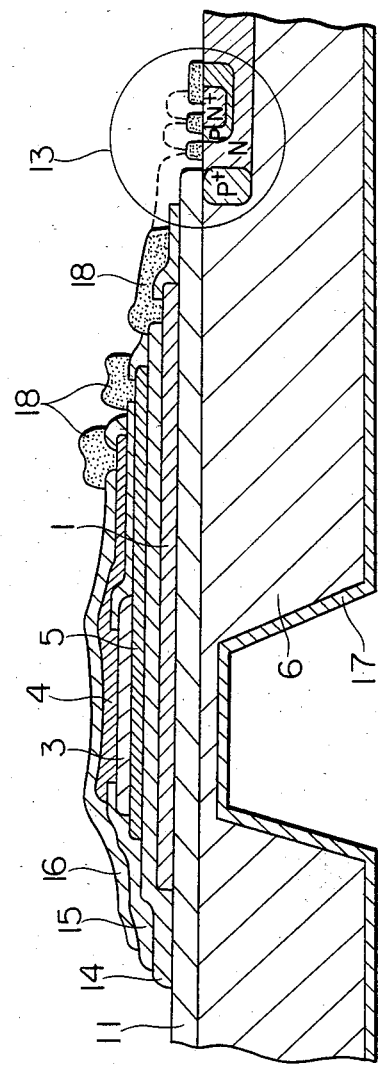
FIG. 19 is a sectional view showing a limiting electric current type oxygen sensor according to still another embodiment of the present invention wherein a processing circuit is formed together with a sensor section on a single substrate.

The sensor side of the base may be brought into contact with the gas to be measured, and the opposite side of the base may be brought into contact with another gas such as air. For this purpose, a hollow cylindrical base 6' one end of which is closed, as shown in FIG. 17, or a hollow cylindrical base 6" having both ends open, as shown in FIG. 19, can be used. Heater 1 is formed on the inner surface of the base 6' or 6". The cathode 5, a thin solid electrolyte film 3, anode 4 and coating 2 are sequentially formed on the outer surface of the base 6' or 6". Reference numeral 12 denotes an insulating film.

Figure 20:
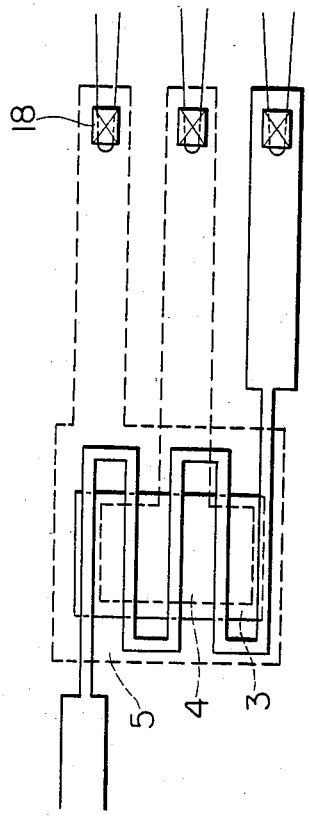
FIG. 20 is a plan view of the oxygen sensor shown in FIG. 19.

In addition, as shown in FIG. 11, the base can be formed by etching to be of bridge or diaphragm type. Therefore, a thin film limiting electric current type sensor with a heater, as shown in FIG. 11, can be formed on a silicon substrate having a processing circuit section including a converter for converting to a voltage the output current detected by a limiting electric current type oxygen sensor, a detector for measuring the electric resistance of the heater and detecting heater temperature, a presetter for setting the heater temperature to a target temperature, a circuit for controlling power supply to the heater, and the circuit for controlling a heating rate of the heater. The sensor of this type is illustrated in FIGS. 19 and 20.

FIG. 19 is a sectional view of the sensor described above, and FIG. 20 is a plan view thereof. A processing circuit section 13 is formed on a part of a silicon substrate 6, and a sensor section is formed on another part thereof and is electrically connected to the processing circuit section 13. The sensor section has a construction such that an $SiO_2$ film 11, heater 1, $Al_2O_3$ film 14, cathode 5, thin electrolyte film 3, anode 4 and so on are sequentially formed on the silicon substrate 6. Reference numerals 15 and 16 denote $Al_2O_3$ films; 17, an $Si_3N_4$ film; and 18, Pt electrodes, respectively.

(Processing Circuit Section)

The processing circuit section will be described in detail with reference to the accompanying drawings.

Figure 21:
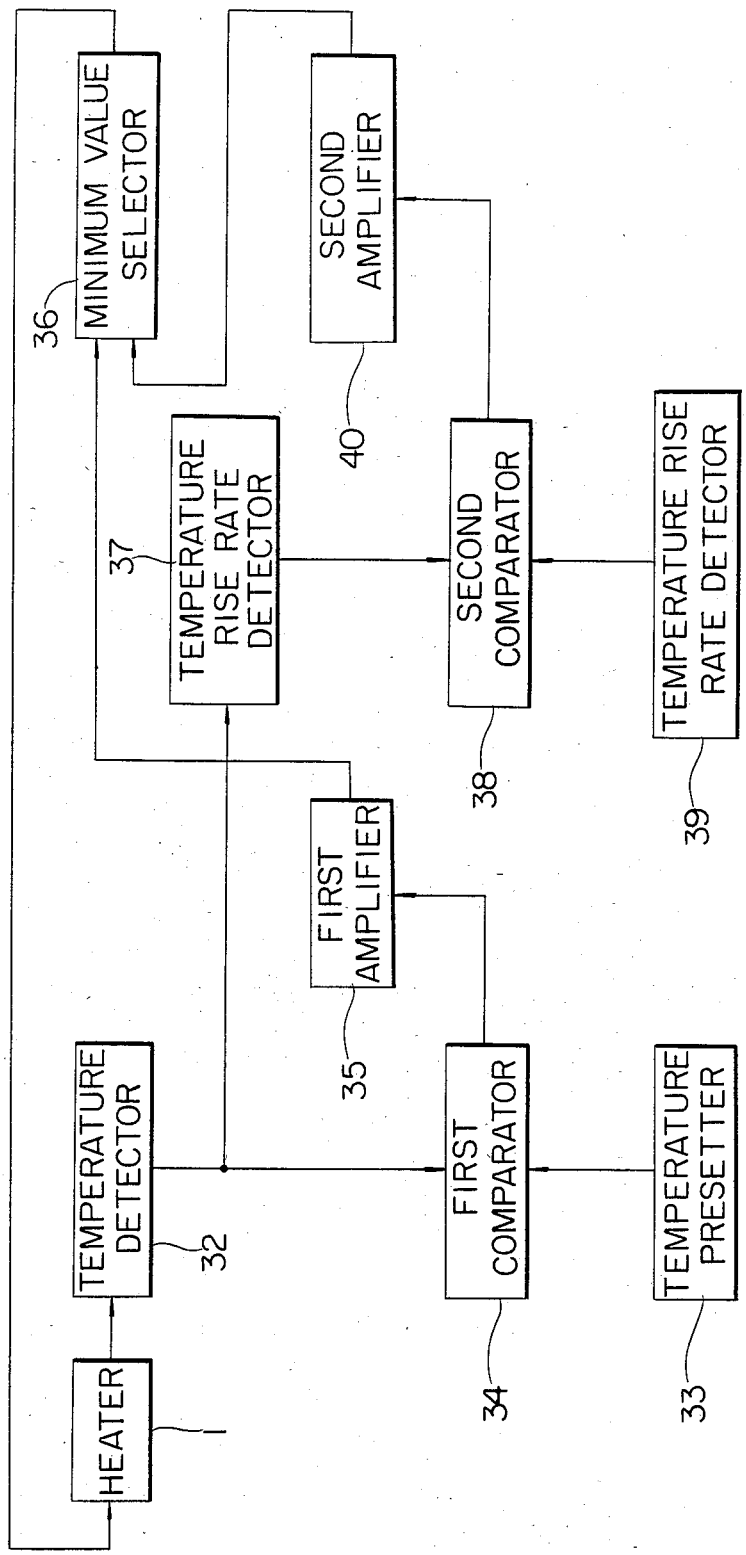
FIG. 21 is a schematic block diagram showing a heater temperature control circuit used in the limiting electric current type oxygen sensor of the present invention.

FIG. 21 is a schematic block diagram of a heater temperature control device to be used in the sensor of the present invention. The output from a temperature detector 32 and the output from a temperature presetter 33 for presetting the sensor temperature are supplied to a first comparator 34. The first comparator 34 compares the outputs which respectively represent the detected temperature and the preset temperature and generates an output which represents a difference therebetween. The output from the first comparator 34 is amplified by a first amplifier 35. An amplified output is supplied to a minimum value selector 36.

Meanwhile, the output from the temperature detector 32 is also supplied to a temperature rise rate detector 37. The temperature rise rate detector 37 detects a rise rate of temperature. A detected output is supplied to one input terminal of a second comparator 38. A temperature rise rate presetter 39 stores preset rise rate data corresponding to the sensors to be used. Proper preset data of the presetter 39 is supplied to the other input terminal of the second comparator 38. The second comparator 38 compares the detected rise rate with the preset rise rate and generates an output which represents a difference therebetween. A difference output is amplified by a second amplifier 40, and an amplified signal is supplied to the minimum value selector 36. The minimum value selector 36 compares the output from the first amplifier 35 with the output from the second amplifier 40 and selects the smaller value. The heater 1 is heated in accordance with the selected value.

In the arrangement described above, at the beginning of heating the actual temperature detected by the temperature detector 32 is much lower than the preset temperature data read out from the temperature presetter 33, so that the output from the first amplifier 35 becomes great. When heating of the heater is controlled in accordance with this value, the temperature rise rate is increased. This rise rate is detected by the temperature rise rate detector 37 and is compared by the second comparator 38 with the preset value read out from the temperature rise rate presetter 39, so that the second comparator 38 generates the difference as described above. The temperature rise rate is greatly increased at the beginning of heating as described above, so that the output from the second comparator 38 is abruptly decreased to be zero. The minimum value selector 36 selects the smaller one of the outputs from the first and second amplifiers 35 and 40. When the detected temperature rise rate comes close to the preset temperature rise rate, the selector 36 selects the output generated from the second amplifier 40 and controls the heater such that the temperature rise rate does not exceed the preset temperature rise rate.

In this manner, when the actual temperature rise rate is about to exceed the preset value, the actual rate is decreased, thereby preventing the actual rate from exceeding the preset value.

When the actual heater temperature comes close to the preset value, the output from the first amplifier 35 is decreased, so that the rise in heater temperature is restricted and hence the heater temperature is held to be constant.

Figure 22:
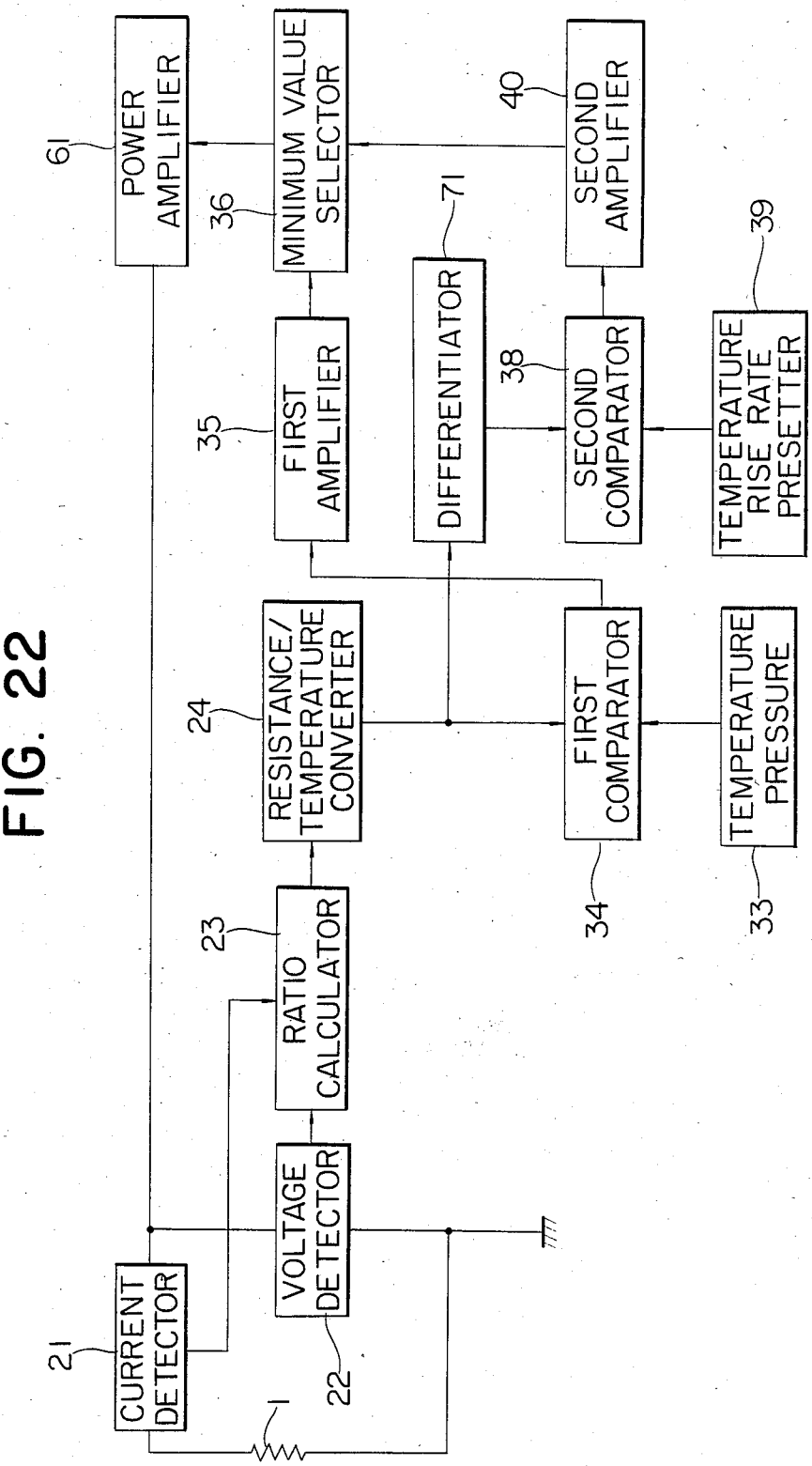
FIG. 22 is a detailed block diagram of the circuit of FIG. 21.

FIG. 22 is a detailed block diagram of the circuit of FIG. 21. An output signal (voltage or current) from the minimum value selector 36 is supplied to a power amplifier 61. An output from the power amplifier 61 is supplied to one end of the heater 1 through a current detector 21. The other end of the heater 61 is properly grounded. A voltage detector 22 is connected between the output terminal of the power amplifier 61 and ground. An output signal (voltage or current) from the voltage detector 22 and an output signal from the current detector 21 are supplied to a ratio calculator 23. An output signal from the ratio calculator 23 is supplied to a resistance/temperature converter 24, an output signal wherefrom is supplied to the first comparator 34 and a differentiator 71. The arrangement of any other part of FIG. 22 is the same as that of FIG. 21.

The operation of the heater control device having the configuration shown in FIG. 22 will be described. The resistance of the heater 1 is the ratio of a voltage E applied thereto and a current I flowing therethrough. A ratio (quotient) of a signal corresponding to the voltage detected by the voltage detector 22 to a signal corresponding to the current detected by current detector 21 is a value corresponding to the resistance of the heater 1.

The resistance of the heater made of platinum (Pt), tungsten (W) or nickel (Ni) increases substantially linearly upon an increase in temperature. Therefore, the linear relationship between the resistance of the heater and the temperature thereof is established. In this manner, the heater temperature can be known without arranging a heat-sensitive element (such as a thermocouple or temperature-sensitive resistor). The resistance/temperature converter 24 can convert the heater resistance (voltage or current signal corresponding to the heater resistance) to a heater temperature (voltage or current signal corresponding to the heater temperature). In addition, the power amplifier 61 amplifies the output signal (voltage or current) from the minimum value selector 36 and generates a voltage or current of a proper level sufficient to heat the heater 1 to the target temperature. This voltage (or current) is applied to the heater 1. The operation of any other part of the circuit of FIG. 22 is the same as that of FIG. 21.

Figure 23:
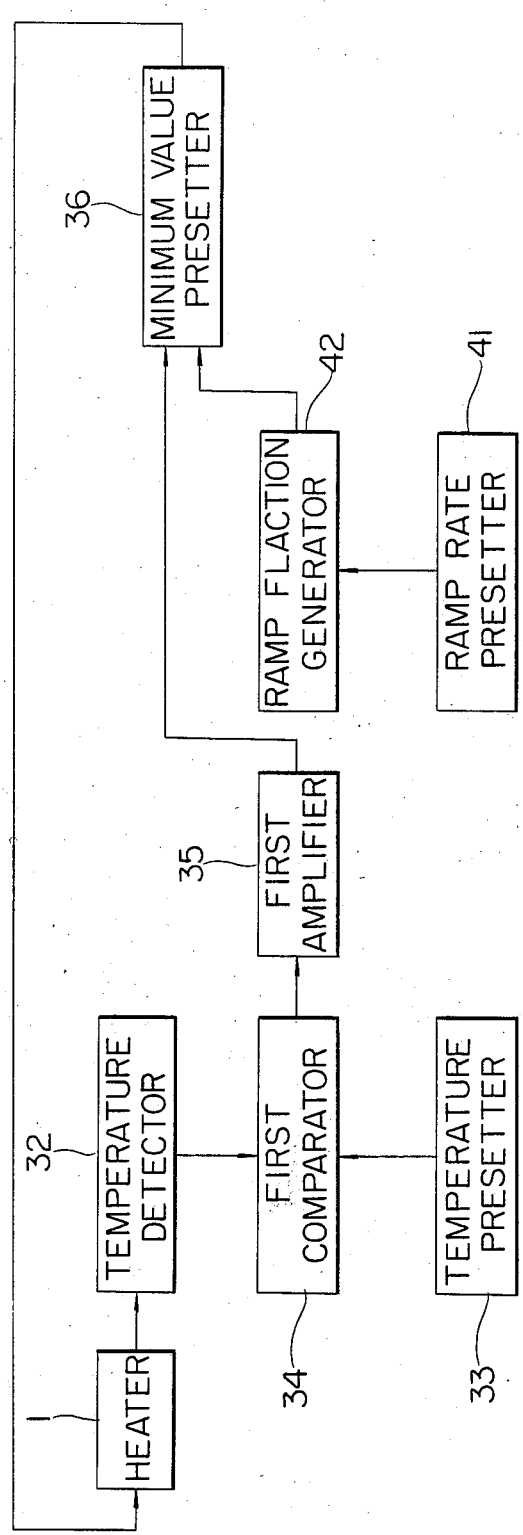
FIG. 23 is a block diagram showing another heater temperature control circuit used in the limiting electric current type oxygen sensor of the present invention.

FIG. 23 shows another processing circuit section to be used for the sensor of the present invention. The circuit arrangement of FIG. 23 is substantially the same as that of FIGS. 21 and 22, except that a ramp rate presetter 41 and a ramp function generator 42 are arranged in place of the temperature rise rate presetter and the temperature rise rate detector, respectively. For this reason, the temperature rise rate at the beginning of heating can be limited in accordance with the power (voltage or current) determined by the ramp function. The circuit of FIG. 23 can be simply arranged as compared with the circuit shown in FIGS. 21 and 22.

Figure 24:
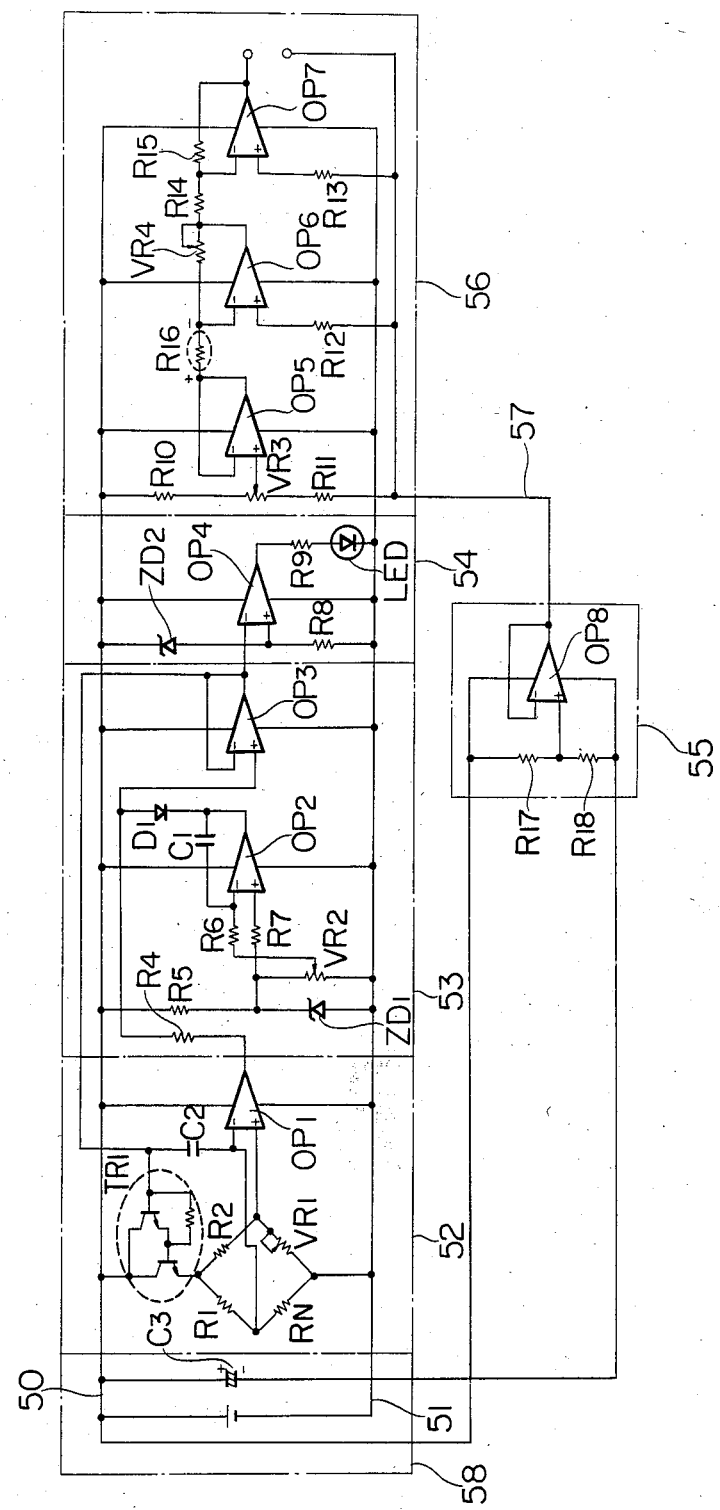
FIG. 24 is a circuit diagram of a processing circuit which comprises a heater temperature control circuit for properly controlling a temperature rise in the heater at the beginning of heating and an oxygen concentration detecting circuit, and which is used in the limiting electric current type oxygen sensor of the present invention.

FIG. 24 shows still another processing circuit section to be used for the sensor of the present invention. This processing circuit section is characterized by a temperature rise control section for controlling temperature rise rate of the heater at the beginning of heating.

Referring to FIG. 24, a Wheatstone bridge circuit having a heater $R_N$ as one side thereof, and resistors $R_1$ and $R_2$ and a variable resistor $VR_1$ as other sides thereof, serves to heat the heater and detect the heater temperature. The common node between the resistors $R_1$ and $R_N$ is connected to the inverting input terminal of an operational amplifier $OP_1$, and the common node between the resistor $R_2$ and the variable resistor $VR_1$ is connected to the noninverting input terminal of the operational amplifier $OP_1$. The output terminal of the operational amplifier $OP_1$ is connected to the anode of a diode $D_1$ through a resistor $R_4$, and also to the noninverting input terminal of an operational amplifier $OP_3$. The cathode of the diode $D_1$ is connected to the output terminal of an operational amplifier $OP_2$. The output from the operational amplifier $OP_3$ is fed back to its inverting input terminal. The output terminal of the operational amplifier $OP_3$ is also connected to the inverting input terminal of an operational amplifier $OP_4$ and to the base of an npn input transistor of a Darlington amplifier $TR_1$. The collectors of the npn input and power transistors of the Darlington amplifier $TR_1$ are connected to a positive power supply line 50. The emitter of the power transistor of the Darlington amplifier $TR_1$ is connected to the common node between the resistors $R_1$ and $R_2$. The common node between the heater $R_N$ and the variable resistor $VR_1$ is connected to a ground (0 V) line 51. One end of a resistor $R_5$ is connected to the positive power supply line 50, and the other end thereof is connected to the cathode of a Zener diode $ZD_1$. The anode of the Zener diode $ZD_1$ is connected to the ground line 51. A variable resistor $VR_2$ is connected across the Zener diode $ZD_1$. The cathode of the Zener diode $ZD_1$ is connected to the noninverting input terminal of the operational amplifier $OP_2$ through a resistor $R_7$. A shunt terminal of the variable resistor $VR_2$ is connected to the inverting input terminal of the operational amplifier $OP_2$ through a resistor $R_6$. The output terminal of the operational amplifier $OP_2$ is connected to its inverting input terminal through a capacitor $C_1$. A capacitor $C_2$ is connected between the base of the npn input transistor of the Darlington amplifier $TR_1$ and the inverting input terminal of the operational amplifier $OP_1$. The cathode of a Zener diode $ZD_2$ is connected to the positive power supply line 50, and the anode thereof is connected to one end of a resistor $R_8$. The common node between this anode and the one end of the resistor $R_8$ is connected to the noninverting input terminal of the operational amplifier $OP_4$. The other end of the resistor $R_8$ is connected to the ground line 51. The output terminal of the operational amplifier $OP_4$ is connected to a light-emitting diode LED through a resistor $R_9$.

The circuit arrangement described above corresponds to a constant temperature control section 52, a temperature rise control section 53 and a temperature rise discrimination section 54. A detector circuit 56 of the limiting electric current type oxygen sensor which detects the oxygen concentration will be described hereinafter.

One end of a resistor $R_{17}$ is connected to the positive power supply line 50, and one end of a resistor $R_{18}$ is connected to the ground line 51. The common node between the other end of each of the resistors $R_{17}$ and $R_{18}$ is connected to the noninverting input terminal of an operational amplifier $OP_8$. The output terminal of the operational amplifier $OP_8$ is connected to its inverting input terminal. The above circuit arrangement corresponds to a center voltage output section 55.

One end of a resistor $R_{10}$ is connected to the positive power supply line 50, and the other end thereof is connected to one end of a variable resistor $VR_3$. The other end of the variable resistor $VR_3$ is connected to the output terminal (via a center voltage line 57) of the operational amplifier $OP_8$ through a resistor $R_{11}$. The shunt output terminal of the variable resistor $VR_3$ is connected to the noninverting input terminal of an operational amplifier $OP_5$. The output terminal of the operational amplifier $OP_5$ is fed back to its inverting input terminal and is also connected to a positive voltage input terminal of a limiting electric current type oxygen sensor $R_{16}$. The negative voltage input terminal of the oxygen sensor $R_{16}$ is connected to the inverting input terminal of an operational amplifier $OP_6$. The noninverting input terminal of the operational amplifier $OP_6$ is connected to the center voltage line 57 through a resistor $R_{12}$. The output terminal of the operational amplifier $OP_6$ is connected to one end and to the shunt terminal of a variable resistor $VR_4$. The other end of the variable resistor $VR_4$ is connected to the inverting input terminal of the operational amplifier $OP_6$.

The noninverting input terminal of an operational amplifier $OP_7$ is connected to the center voltage line 57 through a resistor $R_{13}$. The output terminal of the operational amplifier $OP_6$ is connected to the inverting input terminal of the operational amplifier $OP_7$ through a resistor $R_{14}$. The output terminal of the operational amplifier $OP_7$ is fed back to its inverting input terminal through a resistor $R_{15}$. A voltage between the center voltage line 57 and the output terminal of the operational amplifier $OP_7$ corresponds to an oxygen concentration.

The operation of the processing circuit section described above will now be described.

A temperature is detected by a voltage divided by the resistor $R_1$ and the heater resistor $R_N$. The target temperature is preset by a voltage divided by the resistor $R_2$ and the variable resistor $VR_1$. The operational amplifier $OP_1$ serves to amplify the voltages from the portions corresponding to the temperature detector and the temperature presetter. Even if the positive power supply voltage changes due to a voltage divided by the resistor $R_5$ and the Zener diode $ZD_1$, a constant voltage appears across the Zener diode. This constant voltage is divided by the variable resistor $VR_2$, and a divided voltage is supplied to the resistor $R_6$. The current flowing through the resistor $R_6$ charges the capacitor $C_1$, thereby generating a ramp function. When the output voltage from the operational amplifier $OP_1$ is higher than that from the operational amplifier $OP_2$, a current flows through the diode $D_1$ to increase the voltage at the anode of the diode $D_1$. However, when the output voltage from the operational amplifier $OP_2$ is higher than that from the operational amplifier $OP_1$, no current flows through the diode $D_1$, so that the output voltage from the operational amplifier $OP_1$ has substantially the same level as that at the anode of the diode $D_1$. The operational amplifier $OP_3$ is negatively fed back, so that its output voltage becomes equal to the voltage of its noninverting input terminal. In this sense, the operational amplifier $OP_3$ has a current amplification function. The capacitor $C_1$, the resistor $R_6$, the variable resistor $VR_2$ and the Zener diode $ZD_1$ constitute the ramp rate presetter.

The diode $D_1$ serves to select a lower output voltage of the output voltages from the operational amplifiers $OP_1$ and $OP_2$, and to supply the selected lower voltage to the operational amplifier $OP_3$.

When the heater comprises a resistor which has a positive temperature coefficient, a rise in heater voltage becomes proportional to a rise in heater resistance. For this reason, the bridge circuit including the heater $R_N$, the operational amplifiers $OP_1$ and $OP_2$ and the Darlington amplifier $TR_1$ constitutes a negative feedback circuit. When a difference between the shunt ratio at the left half of the bridge circuit and that at the right half thereof becomes equal to an inverse number of an amplification gain of the circuit as a whole, the circuit can be balanced and becomes steady state. The gain factor of the operational amplifier is as very high as $10^4$ to $10^8$. Therefore, the inverse number becomes as very small as $10^{-4}$ to $10^{-8}$, which can be neglected. Therefore, this negative feedback circuit serves to render the heater resistance constant. The heater resistance proportionally increases in accordance with an increase in heater temperature. When the heater resistance is held to be a given value, the temperature can be held at a predetermined value. In this manner, the temperature control function can be effected.

Since the heater resistance is small at the beginning of heating, an input voltage to the inverting input terminal of the operational amplifier $OP_1$ is smaller than that to the noninverting input terminal thereof. Therefore, the output voltage from the operational amplifier $OP_1$ is high. If the operation amplifier $OP_2$ as the ramp function generator is not provided, the Darlington amplifier $TR_1$ is controlled by this high output voltage, so that a large current flows through the Wheatstone bridge circuit. As a result, the heater $R_N$ is abruptly heated to cause a large thermal distortion due to a large temperature rise, even if the temperature falls within the preset temperature. Therefore, the heater and sensor are degraded and may be damaged.

However, in practice, the operational amplifier $OP_2$ as the ramp function generator is provided, and the output voltage from the operational amplifier $OP_2$ is gradually increased at the beginning of heating in accordance with charging of the capacitor $C_1$. Therefore, at the beginning of heating, the diode $D_1$ is turned on, and the output from the operational amplifier $OP_2$ is used to control the Darlington amplifier $TR_1$ through the operational amplifier $OP_3$. As a result, the heater will not be abruptly heated.

The relationship between the heater heating power and its temperature is established when the power is low-frequency. However, if high-frequency power is used, this relationship cannot be established, so the negative feedback cannot be properly performed. In addition, a phase lag of the transistor or the like also occurs. Oscillation occurs in the positive feedback state, resulting in inconvenience. The capacitor $C_2$ is used to prevent this drawback. The higher the frequency, the lower the impedance of the capacitor $C_2$ becomes, so that the negative feedback gain is increased. As a result, oscillation is prevented to achieve stable circuit operation.

The capacitor $C_3$ of a power supply 58 serves to decrease an impedance of the power supply line when the high-frequency power is supplied. When the impedance of the power supply line is high, an unnecessary coupling occurs through the power supply line, so that oscillation tends to occur in the positive feedback state. It should be noted that the capacitor $C_3$ may be omitted when a power source has an RF impedance.

The operational amplifier $OP_4$ serves to detect whether or not the temperature control section which constitutes a feedback amplifier is properly operated. More particularly, when the output voltages from the operational amplifiers $OP_1$ and $OP_3$, and the emitter voltage of the power transistor of the Darlington amplifier $TR_1$ fall within a predetermined range (a voltage lower than the power supply voltage by not less than 2 V), the output voltage from the operational amplifier $OP_4$ comes close to the power supply voltage, and the light-emitting diode LED is turned on, thereby indicating that the circuit is operating normally.

However, when necessary power for maintaining the heater temperature at the preset temperature cannot be supplied (e.g, when the heat radiation energy of the heater is increased, or when the power supply voltage is decreased), the output voltage from the operational amplifier $OP_3$ becomes higher than that appearing at the common node between the Zener diode $ZD_2$ and the resistor $R_8$. The output voltage from the operational amplifier $OP_4$ then comes close to 0 V, and the light-emitting diode LED is turned off, thereby indicating the abnormal operating state.

On the other hand, when the power supply voltage is excessively high, the power consumption of the Darlington amplifier $TR_1$ is greatly increased. As a result, power loss is increased. In addition, a rise in temperature which is caused by heat radiation becomes a crucial problem. Therefore, when the power supply voltage is set to be a minimum voltage applied to just turn on the light-emitting diode LED, normal temperature control operation and minimum power consumption can be simultaneously realized, resulting in convenience.

The operation of the circuit of the center voltage output section 55 will be described. This circuit generates a voltage obtained such that the power supply voltage is divided by a shunt ratio of the resistors $R_{17}$ and $R_{18}$. Therefore, if a power supply with a center voltage output terminal is used, the center voltage output section can be omitted.

The operation of the circuit of the oxygen concentration detector 56 will now be described. The operational amplifier $OP_5$ comprises a negative feedback circuit and generates a voltage obtained such that the center voltage 57 and the power supply voltage are divided by the resistors $R_{10}$ and $R_{11}$ and the variable resistor $VR_3$. When the limiting electric current type lean sensor $R_{16}$ is used as an exhaust gas sensor, the center voltage is preferably set to be 0.75 V.

A voltage applied to the inverting input terminal of the operational amplifier $OP_6$ is controlled to be set at substantially the center voltage by means of the resistor $R_{12}$. A voltage of 0.75 V is applied across the limiting electric current type lean sensor $R_{16}$. The operational amplifier $OP_6$ and the variable resistor $VR_4$ constitute the current detector. The output voltage of the operational amplifier $OP_6$ on the basis of the center voltage is an inverted voltage of a product of the resistance of the variable resistor $VR_4$ and a current flowing through the limiting electric current type lean sensor $R_{16}$ when a voltage of 0.75 V is applied thereto.

It should be noted that the operational amplifier $OP_7$ comprises an inverting amplifier.

Figure 25:
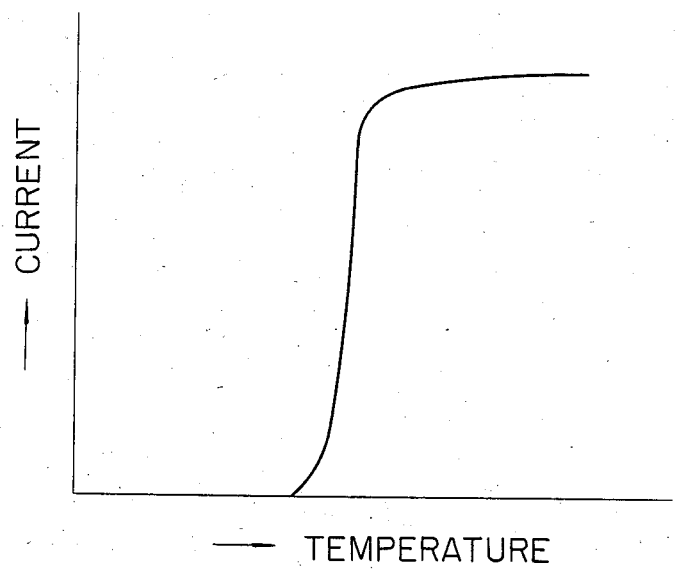
FIG. 25 is a graph showing the relationship between the temperature and the current of a limiting electric current type oxygen sensor (lean sensor) of the present invention when an oxygen concentration is given to be constant.

The relationship between the temperature and the current of the limiting electric current type oxygen sensor at a constant oxygen concentration is shown in FIG. 25.

Figure 26:
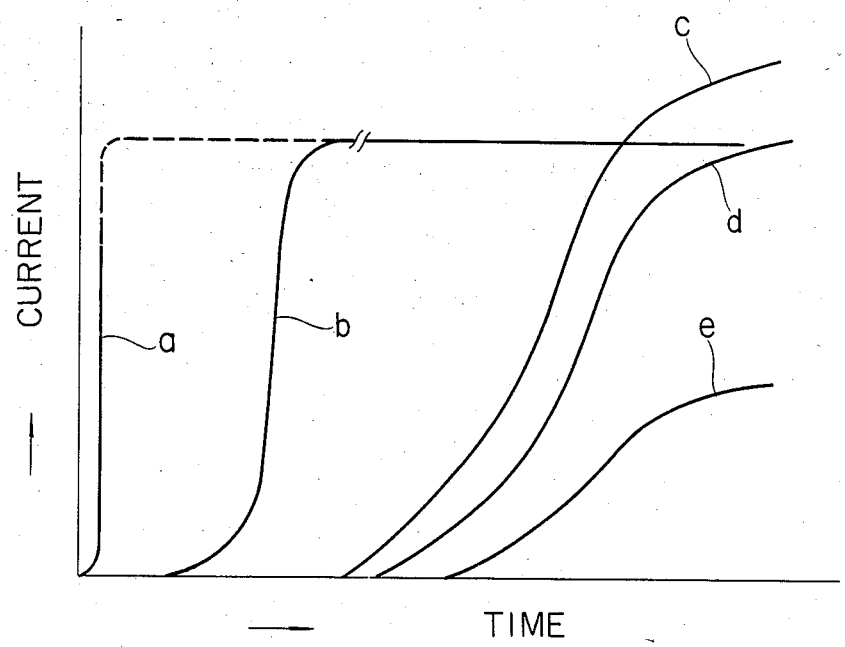
FIG. 26 is a graph showing the relationship between the passage of time of heating the sensor and the output current of the sensor.

FIG. 26 is a graph showing the relationship between the passage of time of heating the sensor and the output current of the sensor.

When contact voltage application or the like is performed to heat the heater instead of performing constant heating control, it takes a long time to heat the heater to the target value, as indicated by curves c, d and e in FIG. 26. In this manner, the sensor cannot be instantaneously started. In addition to this disadvantage, when the heat radiation condition is poor, the temperature is undesirably increased, as indicated by the curve c. In this case, the heater temperature is higher than the preset temperature. On the other hand, when the heat radiation condition is good, the heater temperature becomes low, as indicated by a curve e. The heater temperature cannot reach the preset value.

However, when normal constant temperature heating is performed, an increase in current immediately occurs, as indicated by a curve a. However, the temperature rise rate is excessively high, thereby degrading the heater and the sensor.

However, according to the circuit shown in FIG. 2, the temperature rise rate falls within the allowable range to allow the heater and the sensor to withstand the change in temperature, as indicated by a curve b. As a result, degradation of the heater and the sensor does not occur. At the same time, the heater temperature can reach the target temperature within a short period of time, thereby obtaining a constant current.

Effect of the Invention

As described above in detail, the limiting electric current type oxygen sensor according to the present invention has a simple construction wherein a sensor section is deposited on a base. The manufacturing process can be simplified, and a compact sensor can be prepared. In addition, the heater is formed together with the sensor section on a single base, so that heating power consumption can be decreased.

Furthermore, according to the present invention, a thin solid electrolyte film which has a specific orientation of crystal and a thickness of 0.1 μm to 30 μm is used, so that the electric resistance of the sensor can be greatly decreased to 1/100 to 1/500 that of the conventional sensor. In addition, this thin film can be stably operated, so that a high electric current can be detected. Therefore, accurate, stable oxygen concentration measurement can be performed. Furthermore, the electrode comprises a metal which is capable of decreasing the electrode and the electrolyte interface resistance. As a result, a high-response sensor which can be operated even at low temperatures is obtained.

The oxygen gas permeation path is properly limited by using the dense coating layer, so that the flow rate of oxygen gas is stably determined. In this sense, uniform products having uniform characteristics can be obtained.

Furthermore, the processing circuit section required for sensor operation is formed integrally with the sensor on the single base, thereby omitting lead wires and connectors, and hence decreasing the size of the sensor as a whole.

What is claimed is:

1. A limiting electric current type oxygen sensor comprising an at least partially electrically insulating substrate, a first electrode of a gas-permeable film, a thin solid electrolyte film having a specific orientation of crystal and having a thickness between 0.1 μm and 30 μm, a second electrode of a gas-permeable film, means for determining a diffusion flow rate of a gas flowing therethrough, a portion of said substrate which corresponds to an oxygen concentration detecting portion being removed by etching; said first electrode, said thin solid electrolyte film and said second electrode being sequentially formed on said substate and means for applying positive voltage to one electrode, negative voltage to the other electrode and for detecting electrical current flow through said electrodes.

2. A sensor according to claim 1, wherein said tin solid electrolyte film comprises zirconium oxide stabilized by at least one stabilizer selected from the group consisting of yttrium oxide, ytterbium oxide, gadolinium oxide, magnesium oxide, calcium oxide, and scandium oxide.

3. A sensor according to claim 2, further comprising a thin film heater provided on said substrate, and a processing circuit for processing current flow to determine gas diffusion flow rate wherein said substate comprises silicon and has at least part of said processing circuit formed thereon, said processing circuit including a converter for converting to a voltage output current flow through said electrodes, a circuit for measuring the resistance of said thin film heater and detecting heater temperature, a presetter for presetting a target temperature to control the heater temperature, a circuit for controlling power supply to said thin film heater, and a circuit for controlling heater temperature rise rate, and said porous coating layer comprises a material selected from the group consisting of aluminum oxide, silicon dioxide, spinnel, silicon carbide, and trisilicon tetranitride, and has a porosity of not more than 30% and a thickness of not less than 1 μm.

4. A sensor according to claim 1, wherein said thin solid electrolyte film comprises bismuth trioxide doped with at least one material selected from the group consisting of yttrium oxide, erbium oxide and tungsten trioxide.

5. A sensor according to claim 4, further comprising a thin film heater provided on said substrate, and a processing circuit for processing current flow to determine gas diffusion flow rate wherein said substrate comprises silicon and has at least part of said processing circuit formed thereon, said processing circuit including a converter for converting to a voltage an output current flow through said electrodes, a circuit for measuring the resistance of said thin film heater and detecting heater temperature, a presetter for presetting a target temperature to control the heater temperature, a circuit for controlling power supply to said thin film heater, and a circuit for controlling heater temperature rise rate, and said porous coating layer comprises a material selected from the group consisting of aluminum oxide, silicon dioxide, spinnel, silicon carbide, and trisilicon tetranitride, and has a porosity of not more than 30% and a thickness of not less than 1 μm.

6. A limiting electric current type oxygen sensor comprising an at least partially electrically insulating substrate, a first electrode of a gas-permeable film, a thin and dense solid electrolyte film which has a specific orientation of crystal and a thickness between 0.1 μm and 30 μm, said electrolyte film being devoid of glass-based material, a second electrode of a gas-permeable film, and means for determining a diffusion flow rate of a gas flowing therethrough; said means, said first electrode, said thin and dense solid electrolyte film and said second electrode being sequentially formed on said substrate, and means for applying positive voltage to one electrode, negative voltage to the other electrode and for detecting electrical current flow through said electrodes, thereby enabling said sensor to operate stably even at high temperatures.

7. A limiting electric current type oxygen sensor according to claim 6 wherein said means for determining the gas diffusion flow rate comprises an electrically insulating porous coating layer at least partially covering said substrate, said first electrode, said thin solid electrolyte film and said second electrode.

8. A sensor according to claim 7, wherein said first and second electrodes comprise an element selected from the group consisting of platinum, palladium, silver, and an alloy containing at least one of platinum, palladium and silver as a main constituent.

9. A sensor according to claim 7, wherein said thin solid electrolyte film comprises zirconium oxide stabilized by at least one stabilizer selected from the group consisting of yttrium oxide, ytterbium oxide, gadolinium oxide, magnesium oxide, calcium oxide, and scandium oxide.

10. A sensor according to claim 7, wherein said thin solid electrolyte film comprises bismuth trioxide doped with at least one material selected from the group consisting of yttrium oxide, erbium oxide and tungsten trioxide.

11. A sensor according to claim 7, wherein said porous coating layer comprises a material selected from the group consisting of aluminum oxide, silicon dioxide, spinnel, silicon carbide, and trisilicon tetranitride, and has a porosity of not more than 30% and a thickness of not less than 1 μm.

12. A sensor according to claim 7, further comprising a thin film heater between said substrate and said first electrode through an insulating film.

13. A sensor according to claim 7, further comprising a thin film heater on a surface of said substrate which opposes a surface thereof on which said first electrode, said thin solid electrolyte film and said second electrode are formed.

14. A sensor according to claim 7, further comprising a processing circuit for processing current flow to determine gas diffusion flow rate, said substrate comprising silicon and having at least part of said processing circuit formed thereon.

15. A sensor according to claim 14, further comprising a thin film heater on said substrate, wherein said processing circuit section includes a converter for converting to a voltage an output current generated from said sensor section, a circuit for measuring the resistance of said thin film heater and detecting heater temperature, a presetter for presetting a target temperature to control the heater temperature, a circuit for controlling power supply to said thin film heater, and a circuit for controlling heater temperature rise rate.

16. A sensor according to claim 7, wherein said substrate comprises a cylindrical body; said first electrode, said thin solid electrolyte film and said second electrode are formed on the outer surface of said cylindrical body; and a heater is formed on the inner surface thereof.

17. A sensor according to claim 6, further comprising a dense coating layer formed on the resultant structure of said substrate, said first electrode, said thin solid electrolyte film and said second electrode, said dense coating layer having an opening for limiting a gas flow path.

18. A sensor according to claim 17, wherein said substrate has a dense structure, the one of said first and second electrodes which is a cathode serving as said means for determining the gas diffusion flow rate.

19. A sensor according to claim 17, wherein said substrate has a gas-permeable structure and serves as said means for determining the gas diffusion flow rate.

20. A sensor according to claim 17, wherein said first and second electrodes comprise an element selected from the group consisting of platinum, palladium, silver, and an alloy containing at least one of platinum, palladium and silver as a main constituent.

21. A sensor according to claim 20, wherein
said thin solid electrolyte film comprises zirconium oxide stabilized by at least one stabilizer selected from the group consisting of yttrium oxide, ytterbium oxide, gadolinium oxide, magnesium oxide, calcium oxide, and scandium oxide.

22. A sensor according to claim 21, further comprising a thin film heater provided on said substrate and a processing circuit for processing current flow to determine gas diffusion flow rate, wherein
said substrate comprises silicon and has at least part of a processing circuit formed thereon, said processing circuit including a converter for converting to a voltage an output current flow through said electrodes, a circuit for measuring the resistance of said thin film heater and detecting a heater temperature, a presetter for presetting a target temperature to control the heater temperature, a circuit for controlling power supply to said thin film heater, and a circuit for controlling heater temperature rise rate.

23. A sensor according to claim 20, wherein
said thin solid electrolyte film comprises bismuth trioxide doped with at least one material selected from the group consisting of yttrium oxide, erbium oxide and tungsten trioxide.

24. A sensor according to claim 23, further comprising a thin film heater provided on said substrate, wherein
said substrate comprises silicon, at least part of a processing circuit section being together with a sensor section formed thereon, said processing circuit section being arranged to operate said sensor section, and including converter for converting to a voltage an output current generated from said sensor section, circuit for measuring a resistance of said thin film heater and detecting a heater temperature, a presetter for presetting target temperature to control the heater temperature, a circuit for controlling power supply to said thin film heater, and a circuit for controlling a heater temperature rise rate.

25. A sensor according to claim 17, wherein said thin solid electrolyte film comprises zirconium oxide stabilized by at least one stabilizer selected from the group consisting of yttrium oxide, ytterbium oxide, gadolinium oxide, magnesium oxide, calcium oxide, and scandium oxide.

26. A sensor according to claim 17, wherein said thin solid electrolyte film comprises bismuth trioxide doped with at least one material selected from the group consisting of yttrium oxide, erbium oxide and tungsten trioxide.

27. A sensor according to claim 17, further comprising a thin film heater between said substrate and said first electrode through an insulating film.

28. A sensor according to claim 17, further comprising a thin film heater on a surface of said substrate which opposes a surface thereof which said first electrode, said thin solid electrolyte film and said second electrode are formed.

29. A sensor according to claim 17, further comprising a processing circuit for processing current flow to determine gas diffusion flow rate wherein
said substrate comprises silicon and has at least part of said processing circuit formed thereon, said processing circuit including a converter for converting to a voltage an output current flow through said electrodes, a circuit for measuring the resistance of said thin film heater and detecting a heater temperature, a presetter for presetting a target temperature to control the heater temperature, a circuit for controlling power supply to said thin film heater, and a circuit for controlling heater temperature rise rate.

30. A sensor according to claim 29, further comprising a thin film heater provided on said substrate, wherein said processing circuit section includes a converter for converting to a voltage an output current generated from said sensor section, a circuit for measuring the resistance of said thin film heater and detecting heater temperature, a presetter for presetting a target temperature to control the heater temperature, a circuit for controlling power supply to said thin film heater, and a circuit for controlling heater temperature rise rate.

31. A sensor according to claim 17, wherein said substrate comprises a cylindrical body; said first electrode, said thin solid electrolyte film, said second electrode and said dense coating layer are formed on the outer surface of said cylindrical body; and a heater is formed on the inner surface thereof.

* * * * *